United States Patent
Lee et al.

(10) Patent No.: US 11,213,567 B2
(45) Date of Patent: Jan. 4, 2022

(54) ZAG-DERIVED PEPTIDE AND USE THEREOF

(71) Applicant: L&C Bio Co., LTD., Seongnam-si (KR)

(72) Inventors: Eun Seong Lee, Gwangmyeong-si (KR); Hyung Gu Kim, Seoul (KR); Whan Chul Lee, Seoul (KR); Kee Won Lee, Seoul (KR)

(73) Assignee: L&C Bio Co., LTD., Seongnam-si (KR)

( * ) Notice: Subject to any disclaimer, the term of this patent is extended or adjusted under 35 U.S.C. 154(b) by 0 days.

(21) Appl. No.: 16/652,045

(22) PCT Filed: Sep. 28, 2018

(86) PCT No.: PCT/KR2018/011593
§ 371 (c)(1),
(2) Date: Mar. 29, 2020

(87) PCT Pub. No.: WO2019/066590
PCT Pub. Date: Apr. 4, 2019

(65) Prior Publication Data
US 2020/0246428 A1    Aug. 6, 2020

(30) Foreign Application Priority Data

Sep. 29, 2017  (KR) .................. 10-2017-0127139

(51) Int. Cl.
| | |
|---|---|
| *A61K 38/17* | (2006.01) |
| *A61K 38/10* | (2006.01) |
| *A61K 38/08* | (2019.01) |
| *A61K 38/16* | (2006.01) |
| *A61K 8/64* | (2006.01) |
| *A61P 17/10* | (2006.01) |
| *A61Q 19/00* | (2006.01) |

(52) U.S. Cl.
CPC ............ *A61K 38/1741* (2013.01); *A61K 8/64* (2013.01); *A61P 17/10* (2018.01); *A61Q 19/00* (2013.01)

(58) Field of Classification Search
CPC .... A61K 38/1709; A61K 38/17; A61K 38/10; A61K 38/08; A61K 38/16; A61K 8/64; A61P 17/00; A61Q 19/00
See application file for complete search history.

(56) References Cited

U.S. PATENT DOCUMENTS

| | | | |
|---|---|---|---|
| 7,402,393 B2 * | 7/2008 | Chumakov | ............... A61P 3/04 435/7.1 |
| 2002/0155514 A1 * | 10/2002 | Hale | ................... G01N 33/574 435/7.23 |
| 2007/0054845 A1 * | 3/2007 | Chumakov | ............ C07K 14/47 435/7.1 |

FOREIGN PATENT DOCUMENTS

KR    2017-0114921    10/2017

OTHER PUBLICATIONS

Leal et al, "Is zinc-apha-2-glycoprotein a cardiovascular protective factor for patients undergoing hemodialysis?" Clinica Chimica Acta, 2012, 413: 616-619. (Year: 2014).*
P25311 from UniProt, INtegrated into UniProtKB/Swiss-Prot on May 1, 1992, pp. 1-8. (Year: 1992).*

* cited by examiner

*Primary Examiner* — Julie Ha

(57) ABSTRACT

A zinc-alpha-2-glycoprotein (ZAG) protein-derived peptide according to the present invention shows an expression reducing effect of various immune factors shown in acute or chronic atopic dermatitis, and has a decreased immune response and decreased IgE expression and thus may be used to prevent, treat or improve xeroderma or an abnormal skin barrier function such as atopic dermatitis, an allergic disease or inflammation.

7 Claims, 6 Drawing Sheets

Specification includes a Sequence Listing.

ZAG-DERIVED PEPTIDE AND USE THEREOF

RELATED APPLICATIONS

This application is a National Phase of PCT Patent Application No. PCT/KR2018/011593 having International filing date of Sep. 28, 2018, which claims the benefit of priority of Korean Patent Application No. 10-2017-0127139 filed on Sep. 29, 2017. The contents of the above applications are all incorporated by reference as if fully set forth herein in their entirety.

SEQUENCE LISTING STATEMENT

The ASCII file, entitled 82051SequenceListing.txt, created on Mar. 19, 2029, comprising 11,222 bytes, submitted concurrently with the filing of this application is incorporated herein by reference. The sequence listing submitted herewith is identical to the sequence listing forming part of the international application.

TECHNICAL FIELD AND BACKGROUND OF THE INVENTION

The present invention relates to a zinc-alpha-2-glycoprotein (ZAG) protein-derived peptide and a use thereof.

The epidermis, which is located at the outermost layer of the skin, performs a protective function of preventing a variety of external physical, chemical, and mechanical stimuli and excessive evaporation of moisture through the skin. Such a protective function can be expressed by normally forming and maintaining the stratum corneum consisting of keratinocytes.

Keratinocytes produce natural moisturizing factors and intracellular lipids such as ceramides, cholesterols and fatty acids, such that the stratum corneum serves as a barrier to the outside and thus has a function as a skin barrier.

Xeroderma considered as one of the major diseases of modern society is one of the symptoms caused by abnormal skin barrier functions. Recently, due to various reasons such as environmental pollution, an increasingly dry environment such as a high-rise building, an increase in social stress, excessive bathing culture, dermal aging, etc., the occurrence of xeroderma is gradually increasing, and cases in need of treatment because of severe symptoms are continuously increasing. Atopic dermatitis is also known to result from xeroderma, more fundamentally, an abnormal skin barrier function as a major cause.

Atopic dermatitis is a chronic, recurrent skin disease, and an immune disease involving genetic and environmental factors that shows an incidence of 20% in infancy and early childhood and 1 to 3% in adults. Atopic dermatitis is accompanied by chronic xeroderma and severe pruritus and easily induces dermatitis due to various types of stimuli. When the atopic symptoms become severe, atopic dermatitis develops to subacute lesions of erythematous rashes accompanied by effusion, and chronic lesions that make the skin thicker.

The main pathological changes in atopic dermatitis are abnormal immunological responses and abnormal skin barrier responses. The activity of a type 2 helper T cell, a dendritic cell or an eosinophil, which is caused by a specific allergen, leads to an inflammatory reaction, also resulting in abnormalities of the skin barrier. In addition, 80 to 90% of atopic dermatitis patients have an increased immunoglobulin E level in serum, and particularly, when accompanied by respiratory atopy such as allergic rhinitis or asthma, a high immunoglobulin E level in serum is shown.

As a therapeutic method for atopic dermatitis, immunotherapy and drug therapy are carried out. Typically used drugs include steroids, calcineurin inhibitors, immunomodulators, antihistamines, etc. Topical preparations, for example, a steroid and a calcineurin inhibitor, may have a short-term effect, but cause side effects such as skin atrophy, vasodilation, etc. in the long-term application. An antihistamine, which is a systemic oral preparation, has an insignificant effect. In addition, to restore a dry and broken skin barrier, moisturizers using ceramide are used in the pharmaceutical and cosmetic fields. Despite these many drug therapies, a suitable therapeutic method for atopic dermatitis has not yet been identified.

Patent Document 1 (Korean Patent Application No. 10-2017-0028169) relates to a patent that discloses uses of the ZAG protein for the improvement in xeroderma or a skin barrier function and an antiallergic use thereof. The present invention identifies a ZAG protein-derived peptide which is highly effective in xeroderma, improvement in the skin barrier and, particularly, resistance to an allergic reaction and confirms the relevant effects.

PRIOR ART DOCUMENT

Patent Document

1. Korean Patent Application No. 10-2017-0028169

SUMMARY OF THE INVENTION

The present invention is directed to providing a zinc-alpha-2-glycoprotein (ZAG) protein-derived peptide and a use thereof.

The inventors found a ZAG protein-derived peptide highly effective in improvement in xeroderma and skin barrier function, and resistance to an allergic reaction and an inflammatory response.

Therefore, the present invention provides a use of a ZAG protein-derived peptide for preparing a drug or cosmetic for preventing, treating or improving xeroderma or an abnormal skin barrier function, use of a ZAG protein-derived peptide for preparing an antiallergic drug or cosmetic, and use of a ZAG protein-derived peptide for preparing an anti-inflammatory drug or cosmetic.

In addition, the present invention provides a pharmaceutical composition for preventing, treating or improving xeroderma or an abnormal skin barrier function, which includes the ZAG protein-derived peptide as an active ingredient, a cosmetic composition for improving xeroderma or an abnormal skin barrier function, which includes the ZAG protein-derived peptide as an active ingredient, an antiallergic pharmaceutical composition including the ZAG protein-derived peptide as an active ingredient, an antiallergic cosmetic composition including the ZAG protein-derived peptide as an active ingredient, and an anti-inflammatory pharmaceutical or cosmetic composition including the ZAG protein-derived peptide as an active ingredient.

The present invention also provides a method of preventing, treating or improving xeroderma or an abnormal skin barrier function, which comprises administering a therapeutically or physiologically effective amount of a ZAG protein-derived peptide into a subject in need thereof, a method of preventing, treating or improving an allergic disease, which comprises administering a therapeutically or physiologically effective amount of a ZAG protein-derived peptide into a subject in need thereof, and a method of preventing, treating or improving inflammation, which comprises administering a therapeutically or physiologically effective amount of a ZAG protein-derived peptide into a subject in need thereof.

The term "ZAG protein-derived peptide" used herein refers to an active peptide of the amino acid sequence of the ZAG protein, which has an effect of improving xeroderma or an abnormal skin barrier function. In one embodiment of the present invention, the "ZAG protein-derived peptide" may be a peptide consisting of an amino acid sequence of 10-mer or more and 50-mer or less, which includes a fragment of the ZAG protein. The fragment of the ZAG protein included in the "ZAG protein-derived peptide" may consist of a sequence of 10-mer or more and 50-mer or less, particularly, a sequence of 10-mer to 30-mer, 10-mer to 25-mer, 10-mer to 20-mer or 10-mer to 15-mer contiguous amino acids, among the amino acid sequence constituting the ZAG protein.

In one embodiment of the present invention, the fragment of the ZAG protein may consist of a 10-mer to 30-mer contiguous amino acid sequence among the amino acid sequence constituting the ZAG protein.

In one embodiment of the present invention, the fragment of the ZAG protein may consist of any one amino acid sequence selected from SEQ ID NOs: 1 to 19.

In one embodiment of the present invention, the fragment of the ZAG protein may consist of any one amino acid sequence selected from SEQ ID NOs: 20 to 26.

The "ZAG protein-derived peptide" used herein is interchangeably used with the "fragment of the ZAG protein" in a part of the description. For example, the ZAG protein-derived peptide may consist of any one amino acid sequence selected from SEQ ID NOs: 1 to 19. Alternatively, the ZAG protein-derived peptide may consist of any one amino acid sequence selected from SEQ ID NOs: 20 to 26.

The following examples disclose a ZAG protein-derived peptide effective in improvement in xeroderma and skin barrier function, and resistance to an allergic reaction or an inflammatory response. The "ZAG protein-derived peptide" used herein may be, but is not limited to, ZAG protein-derived peptides of Z1 to Z18 (represented by SEQ ID NOs: 1 to 18, respectively), which is shown in Table 1. It was confirmed that these peptides have efficacy on improvement in xeroderma or skin barrier function, and resistance to an allergic reaction and an inflammatory response. Particularly, it was confirmed that the ZAG protein-derived peptide of Z3 has an effect of reducing an immune response at the same level as that of the ZAG protein, resulting in an atopic dermatitis improvement effect. In one embodiment of the present invention, the "ZAG protein-derived peptide" may include ZAG protein-derived peptides of Z20mer-1, Z20mer-2, Z20mer-3, Z15mer-1, Z15mer-2, Z15mer-3 and Z15mer-4 (represented by SEQ ID NOs: 20 to 26, respectively), which is shown in Table 4.

The peptides of Z1 to Z18, or Z20mer-1, Z20mer-2, Z20mer-3, Z15mer-1, Z15mer-2, Z15mer-3, and Z15mer-4 are merely examples of the ZAG protein-derived peptide according to the present invention, and the "ZAG protein-derived peptide" may be a partial sequence of Z1 to Z18, or Z20mer-1, Z20mer-2, Z20mer-3, Z15mer-1, Z15mer-2, Z15mer-3, and Z15mer-4. Alternatively, the ZAG protein-derived peptide may be a peptide prepared by combining some of the peptides.

The "ZAG protein-derived peptide" according to the present invention may include an amino acid sequence having 75% or more, preferably, 80% or more, more preferably 90% or more, and most preferably, 95% or more homology with an amino acid sequence of the Z1 to Z18 peptides, or the Z20mer-1, Z20mer-2, Z20mer-3, Z15mer-1, Z15mer-2, Z15mer-3, and Z15mer-4 peptides.

In addition, the "ZAG protein-derived peptide" may include a cell-permeable peptide, a targeting sequence, a tag, a labeled residue, and an amino acid sequence prepared for a specific purpose of increasing a half-life or the stability of the peptide, as well as an amino acid sequence constituting an active peptide, that is, the fragment of the ZAG protein. For example, the present invention may be a fusion peptide in which a cell-permeable peptide, a targeting sequence, a tag, a labeled residue, and an amino acid sequence prepared for a specific purpose of increasing a half-life or the stability of the peptide is fused to any one end of one of the peptides of Z1 to Z18 or the peptides of Z20mer-1, Z20mer-2, Z20mer-3, Z15mer-1, Z15mer-2, Z15mer-3, and Z15mer-4.

In addition, the "ZAG protein-derived peptide" according to the present invention may further include a functional variant thereof. The functional variant includes biological equivalents of the "ZAG protein-derived peptide" described herein. For example, to further improve the binding affinity of the peptide and/or other biological properties, an additional change may be imparted to the amino acid or polynucleotide sequence of the peptide. Such modifications include the deletion, insertion, and/or substitution of a residue of the amino acid sequence of an antibody, and are made based on the relative similarity of amino acid side-chain substituents, for example, hydrophobicity, hydrophilicity or a charge size. According to the size, shape, and type of an amino acid side chain substituent, it can be seen that all of arginine, lysine, and histidine are positively-charged residues; alanine, glycine and serine have similar sizes; and phenylalanine, tryptophan and tyrosine are similar types. Therefore, based on these considerations, arginine, lysine and histidine; alanine, glycine and serine; and phenylalanine, tryptophan and tyrosine may be biologically functional equivalents.

In addition, the peptide of the present invention may be obtained by various methods widely known in the art. As an example, the peptide may be prepared using polynucleotide recombination and a protein expression system, an in vitro synthesis method through chemical synthesis such as peptide synthesis, or a cell-free protein synthesis method.

In addition, to achieve better chemical stability, reinforced pharmacological properties (half-life, absorbability, potency, efficacy, etc.), modified specificity (e.g., broad biological active spectrum), and reduced antigenicity, a protecting group may be bound to the N- or C-terminus of the peptide. Preferably, the protecting group may be an acetyl group, a fluorenyl methoxy carbonyl group, a formyl group, a palmitoyl group, a myristyl group, a stearyl group or polyethylene glycol (PEG), but may include any component that can modify, particularly, improve the stability of the peptide without limitation. The term "stability" used herein means storage stability (e.g., room temperature storage stability) as well as in vivo stability for protecting the peptide of the present invention from the in vivo attack of a protease.

The "ZAG protein-derived peptide" of the present invention may be included, in the pharmaceutical composition or cosmetic composition, at 0.0001 to 50 wt % with respect to the total weight of the composition, but the content is not limited thereto. The pharmaceutical composition or cosmetic composition according to the present invention may further contain one or more types of active ingredients exhibiting the same or similar function, in addition to the ZAG protein-derived peptide.

Meanwhile, the ZAG protein-derived peptide of the present invention may be delivered into a subject by a pharmaceutically, physiologically or cosmetologically acceptable carrier such as a colloidal suspension, a powder, saline, a lipid, a liposome, a microsphere, or a nano-spherical particle. The peptide may form a complex with or may be associated with a delivery means, and may be delivered into the body using a delivery system known in the art, such as a lipid, a liposome, a micro particle, a polymer, a condensation reagent, a polysaccharide, a polyamino acid, a dendrimer, saponin, an adsorption-enhancing substance or a fatty acid.

In addition, the pharmaceutically, physiologically or cosmetologically acceptable carrier may include lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil, which is conventionally used in preparation, but the present invention is not limited thereto. In addition, the peptide may further include a lubricant, a wetting agent, a sweetening agent, a flavoring agent, an emulsifier, a suspending agent, a preservative or the like, as well as the above-mentioned components.

The term "xeroderma" used herein means all symptoms caused by skin dryness due to a lack of moisture in the skin. The xeroderma used herein may be any symptom caused by skin dryness due to a lack of moisture in the skin, and the type or severity of the specific symptom is not particularly limited.

The term "skin barrier function" used herein means all functions of the skin, particularly, the stratum corneum of the epidermis, acting as a barrier to the outside, such as preventing evaporation of moisture to the outside and the entry of a material from the outside, and the term "abnormal skin barrier function" used herein means all conditions in which there is a possibility of degrading or damaging, or the need of preventing the skin barrier function, as well as a condition in which the skin barrier function is degraded or damaged. The abnormal skin barrier function in the specification may be any symptom caused by degradation or damage of the skin barrier function and the type or severity of a specific symptom is not particularly limited.

In one embodiment of the present invention, a disease exhibiting xeroderma or an abnormal skin barrier function may be atopic dermatitis. The ZAG protein-derived peptide according to the present invention was confirmed to have an excellent effect in the prevention, treatment or improvement of atopic dermatitis.

Moreover, the inventors found that the levels of various inflammatory cytokines and histamine, as well as Th2 cells involved in various immune and inflammatory responses thereby, can be reduced by treating a surface with the ZAG protein. The inventors also found that the ZAG protein increases the level of regulatory T (Treg) cells, which are immunoregulatory cells.

Here, the inflammatory cytokines and the Treg cells may be involved in the development of an allergic disease, particularly, atopic dermatitis. Particularly, the inventors found that the levels of IL-4, IL-5, and IL-13 secreted from Th2 cells and the level of IL-17 secreted from Th17 cells greatly increase in the blood of an atopic dermatitis patient. Here, the increase in IL-17 level may be one of the characteristics of immunological abnormalities. Therefore, a mechanism of reducing the expression level of inflammatory cytokines, particularly, the reduction in the levels of Th2 cell- and Th17 cell-related cytokines, suppresses an inflammatory response, which may be the key point in the prevention and treatment of atopic dermatitis and allergic diseases.

Further, the Treg cells may be lower at lesion sites of atopic dermatitis than in a normal person. Here, the Treg cells are immunoregulatory cells, which may not only have a role in priming of dendritic cells acting on Th1, Th2, and Th17 cells, but also a role in suppressing an inflammatory response, directly suppress the activity of allergen-specific Th2 cells, such that the production of essential cytokines, including IL-4, IL-5, and IL-13, may be minimized during the effector stage of an allergic reaction. In addition, the Treg cells may directly act on mast cells, basophils and eosinophils to inhibit inflammation and interact with tissue cells, thereby playing a critical role in tissue reorganization, and may directly affect B cells to inhibit the production of allergen-specific IgE and induce the production of IgG4. Therefore, a mechanism of improving the function of the Treg cells or increasing levels thereof may be crucial for the inhibition of an immune response, or an inflammatory response caused thereby. Further, such a mechanism may be crucial for the prevention and treatment of an allergic disease, particularly, atopic dermatitis.

Therefore, the inventors recognized that the ZAG protein capable of regulating the levels of inflammatory cytokines and Treg cells may be provided to an antiallergic pharmaceutical composition and an anti-inflammatory pharmaceutical composition, which are effective in the prevention or treatment of allergic disease.

Accordingly, the present invention also provides an antiallergic pharmaceutical or cosmetic composition, a pharmaceutical or cosmetic composition for preventing, treating or improving an allergic disease and an anti-inflammatory pharmaceutical or cosmetic composition, which include a ZAG protein-derived peptide.

The antiallergic pharmaceutical composition, pharmaceutical composition for preventing or treating allergic disease, and anti-inflammatory composition according to an exemplary embodiment of the present invention may be used as a composition for preventing or treating various allergic diseases. For example, the antiallergic pharmaceutical composition may be used to prevent or treat allergic diseases including anaphylaxis, allergic rhinitis, asthma, atopic dermatitis, insect allergies, food allergies, drug allergies, and urticaria. More preferably, the antiallergic pharmaceutical composition according to an exemplary embodiment of the present invention may be effective for use as a composition for preventing or treating atopic dermatitis, but the present invention is not limited thereto. In addition, the anti-inflammatory pharmaceutical composition including the ZAG protein-derived peptide according to an exemplary embodiment of the present invention may reduce an inflammatory cytokine level to inhibit an inflammatory response, and therefore may be effective against inflammatory skin disease, particularly, atopic dermatitis.

The term "prevention" used herein refers to all actions of inhibiting or delaying 'xeroderma', 'abnormal skin barrier function', 'allergic disease or allergy' or 'inflammation' by administering the pharmaceutical or cosmetic composition including a ZAG protein-derived peptide according to the present invention.

The term "treatment" used herein refers to all actions involved in alleviating or beneficially changing symptoms of 'xeroderma', 'abnormal skin barrier function', 'allergic disease or allergy' or 'inflammation' by administering the pharmaceutical or cosmetic composition including a ZAG protein-derived peptide according to the present invention.

The term "improvement" used herein refers to all types of actions of alleviating symptoms of 'xeroderma', 'abnormal skin barrier function', 'allergic disease or allergy' or 'inflammation' by administering the pharmaceutical or cosmetic composition including a ZAG protein-derived peptide according to the present invention.

The "subject" used herein refers to a subject in need of the prevention, treatment, and improvement of 'xeroderma', 'abnormal skin barrier function', 'allergic disease or allergy' or 'inflammation', and more specifically, a mammal such as a human or a non-human primate, a mouse, a rat, a dog, a cat, a horse or a cow.

The ZAG protein-derived peptide may be administered to a subject parenterally or orally. Since the ZAG protein-derived peptide may be used for preventing, treating or improving 'xeroderma', 'abnormal skin barrier function', 'allergic disease or allergy' or 'inflammation', it may be prepared as a pharmaceutical or cosmetic composition that can be applied parenterally, particularly, to the skin, and topically administered, but the present invention is not limited thereto. For example, the ZAG protein-derived peptide may be prepared in the form of an ointment, a gel, a cream or a lotion. The type of topical administration may be, for example, application on the skin, transdermal administration using microneedles, or intradermal injection, but the present invention is not limited thereto. For example, the composition is preferably applied on the skin or a patch containing the composition is preferably attached onto the skin.

The composition may further include a pharmacologically or physiologically acceptable carrier, excipient or diluent, as well as the above-described ZAG protein-derived peptide for administration. Examples of the suitable carrier, excipient, and diluent that can be included in the composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. When the composition is formulated, a conventional filler, extender, binder, disintegrant, surfactant, anti-coagulant, lubricant, wetting agent, fragrance, emulsifier or preservative may be further included.

The formulation of the composition may include a solid, an emulsion (including a microemulsion), a suspension, a cream, a lotion, a gel, a powder, or another typical solid or liquid composition used to be applied to the skin and other tissues to which the composition may be applied. Such a composition may additionally include an antimicrobial agent, a moisturizer, a hydration agent, a penetration agent, a preservative, an emulsifier, natural oil or synthetic oil, a solvent, a surfactant, a detergent, a gelling agent, an emollient, an antioxidant, a fragrance, a filler, a thickener, a wax, a deodorant, a dyestuff, a colorant, a powder, a viscosity-controlling agent and water, and may optionally contain an anesthetic, an anti-itching agent, a botanical extract, a conditioning agent, a darkening or lightening agent, glitter, a humectant, mica, a mineral, a polyphenol, a silicone or a derivative thereof, a sunblock, a vitamin, and a phytomedicine.

In one embodiment of the present invention, a cosmetic composition including the ZAG protein-derived peptide may be provided, and specifically, it may be a cosmetic composition for improving atopic dermatitis, an anti-allergic cosmetic composition or an anti-inflammatory cosmetic composition. The cosmetic composition may have a form selected from the group consisting of a suspension, an emulsion, a gel, and a paste, but the present invention is not limited thereto.

The dose of the composition varies according to the body weight, age, sex, health condition, and diet of a subject, administration time, an administration method, an excretion rate and the severity of a disease. A daily dose may be approximately 0.001 to 100 mg/kg, for example, 0.01 to 10 mg/kg, but the present invention is not limited thereto. The composition may be administered once to several times a day.

The present invention provides a method of preventing, treating or improving xeroderma or an abnormal skin barrier function by administering a therapeutically or physiologically effective amount of a ZAG protein-derived peptide to a subject.

Advantageous Effects of Invention

It can be confirmed that a ZAG protein peptide according to the present invention has efficacy in reducing an immune response acting on acute or chronic atopic dermatitis to improve atopic dermatitis, and the ZAG protein peptide can be used to prevent, treat or improve xeroderma such as atopic dermatitis, an abnormal skin barrier function, an allergic disease or inflammation by reducing an immune response or the expression of IgE.

DESCRIPTION OF SPECIFIC EMBODIMENTS OF THE INVENTION

Figure 1A:
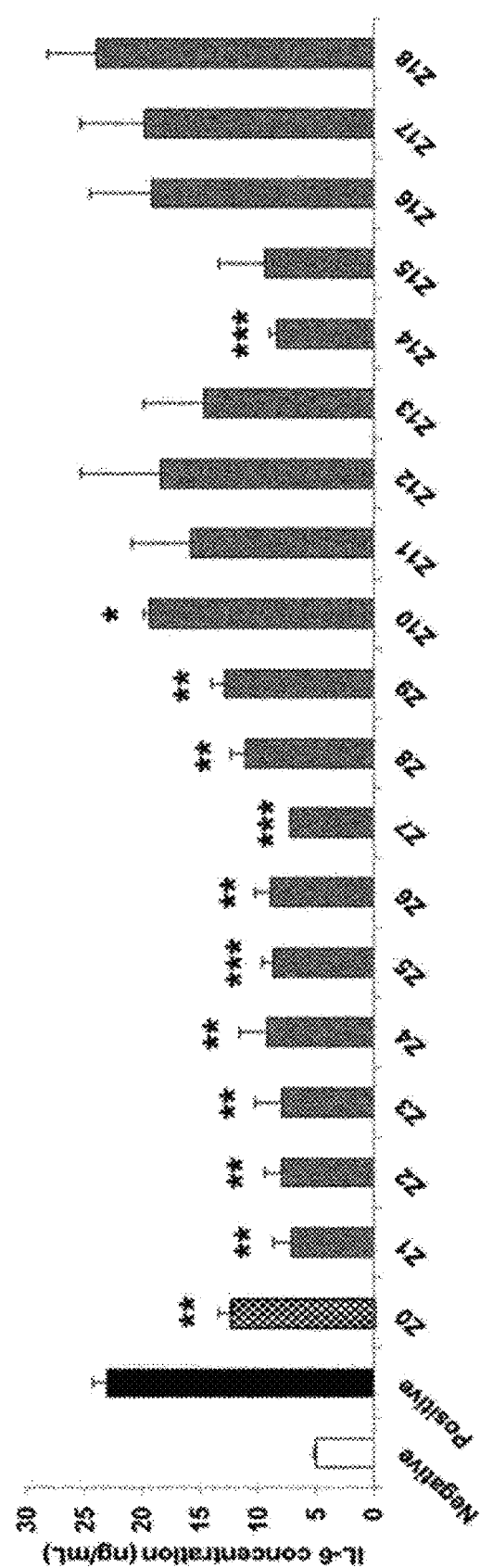
FIGS. 1A, 1B, 1C, 1D and 1E show the result of in vitro efficacy testing of each peptide against atopic dermatitis. (a) is the result for RAW 264.7 macrophages, (b) is the result for RBL-2H3 mast cells, (c) is the result for keratinocytes, (d) is the result for B lymphocytes, and (e) is the result for T lymphocytes.

Hereinafter, the advantages and features of the present invention and the methods of accomplishing the same will become apparent with reference to the detailed description of exemplary embodiments and the accompanying drawings. However, the present invention is not limited to the exemplary embodiments disclosed below, and may be embodied in many different forms. These exemplary embodiments are merely provided to complete the disclosure of the present invention and fully convey the scope of the present invention to those of ordinary skill in the art, and the present invention should be defined by only the accompanying claims.

Preparation Example 1. Synthesis and Isolation of Peptide

To identify a peptide including an active site in the ZAG protein, in the entire sequence of 298 amino acids (Gen- Bank: AAH05306.1; SEQ ID NO: 19), 18 peptide candidate groups (Z1 to Z18, SEQ ID NOs: 1 to 18, respectively) were established such that 15 amino acids overlapped. Each peptide was prepared by solid-phase peptide synthesis. It was confirmed by HPLC analysis that the synthesized peptide of the present invention has a purity of 90% or more. The molecular weight of the purified peptide was confirmed by mass spectrometry (Table 1: Peptide candidate groups and amino acid sequences used to identify ZAG protein active site).

TABLE 1

| Name of peptide | M.W. (g/mol) | Sequence | SEQ ID NO. |
|---|---|---|---|
| Z1 | 3443.74 | QENQDGRYSLTYIYTGLSKHVEDVPAFQAL | 1 |
| Z2 | 3589.04 | GSLNDLQFFRYNSKDRKSQPMGLWRQVEGM | 2 |
| Z3 | 3751.07 | EDWKQDSQLQKAREDIFMETLKDIVEYYND | 3 |
| Z4 | 3485.73 | SNGSHVLQGRFGCEIENNRSSGAFWKYYYD | 4 |
| Z5 | 3520.96 | GKDYIEFNKEIPAWVPFDPAAQITKQKWEA | 5 |
| Z6 | 3604.16 | EPVYVQRAKAYLEEECPATLRKYLKYSKNI | 6 |
| Z7 | 3370.85 | LDRQDPPSVVVTSHQAPGEKKKLKCLAYDF | 7 |
| Z8 | 3344.62 | YPGKIDVHWTRAGEVQEPELRGDVLHNGNG | 8 |
| Z9 | 3296.64 | TYQSWVVVAVPPQDTAPYSCHVQHSSLAQP | 9 |
| Z10 | 3396.73 | GLSKHVEDVPAFQALGSLNDLQFFRYNSKD | 10 |
| Z11 | 3661.07 | RKSQPMGLWRQVEGMEDWKQDSQLQKARED | 11 |
| Z12 | 3535.93 | PFDPAAQITKQKWEAEPVYVQRAKAYLEEE | 12 |
| Z13 | 3457.97 | CPATLRKYLKYSKNILDRQDPPSVVVTSHQ | 13 |
| Z14 | 3478.88 | IFMETLKDIVEYYNDSNGSHVLQGRFGCEI | 14 |
| Z15 | 3691.00 | ENNRSSGAFWKYYYDGKDYIEFNKEIPAWV | 15 |
| Z16 | 3420.95 | APGEKKKLKCLAYDFYPGKIDVHWTRAGEV | 16 |
| Z17 | 3306.57 | QEPELRGDVLHNGNGTYQSWVVVAVPPQDT | 17 |
| Z18 | 3215.56 | AVPPQDTAPYSCHVQHSSLAQPLVVPWEAS | 18 |

Example 1. Selection of Peptide by In Vitro Efficacy Test Against Atopic Dermatitis To select an amino acid sequence corresponding to a key active site of ZAG having efficacy in the alleviation of atopic symptoms from 18 peptide candidate groups, an atopic dermatitis efficacy test was performed. Five types of immune-related cells were treated with ZAG peptide candidate groups (Z1-Z18, SEQ ID NOs: 1 to 18, respectively) and the ZAG protein (Z0, SEQ ID NOs: 19) at a concentration of 1 μg/mL for 24 hours, and then treated with a stimulator suitable for each cell line for the listed time to confirm an immune response. The experiment was performed with a group treated with only a stimulator as a positive control experimental group, and a group treated with only a vehicle without a stimulator as a negative control experimental group (Table 2: Efficacy test method for atopic dermatitis). An inflammatory response-related enzyme used as a stimulator is produced by immune cells, and histamine initiates an inflammatory response. The immune cells migrating to a damaged region release cytokines such as tumor necrosis factor-α (TNF-α) and interleukin-6 (IL-6) to directly lyse foreign invasive substances or collect other immune cells to initiate an inflammatory response. An efficacy test using inflammation-inducing materials, interferon-γ and skin inflammation-related factor CCL-17/thymus- and activation-regulated chemokine (TARC) was also performed to confirm an immune response.

TABLE 2

| Cell Type | Stimulator concentration | Vehicle (diluent) | Time duration | Inflammatory target |
|---|---|---|---|---|
| RAW 264.7 (Macrophage) | LPS 0.1 μg/mL | PBS | 24 hours | IL-6 |
| RBL-2H3 (Mast cell) | PMA 1 μg/mL, A23187 1 μg/mL | DMSO | 12 hours | Histamine |
| RPMI 1788 (B-lymphocyte) | LPS 0.1 μg/mL | PBS | 24 hours | IgE |
| HaCaT (Keratinocyte) | TNF-α 0.4 μg/mL, IFN-γ 0.4 μg/mL | PBS | 24 hours | CCL17/ TARC |
| T-lymphocyte | IL-2 50 ng/mL | PBS | 12 hours | IL-4 |

Example 1-1. Atopic Dermatitis Efficacy Test Using Macrophages

Macrophages (RAW 264.7 cells) were treated with a stimulator LPS at a concentration of 0.1 μg/mL for 24 hours, and then the concentration of IL-6 released in a cell culture medium was confirmed by ELISA assay. In the experimental groups treated with Z0, Z1 to Z10, and Z14, compared with an experimental group only treated with a stimulator, the IL-6 concentration was significantly decreased (FIG. 1A).

Example 1-2. Atopic Dermatitis Efficacy Test Using Mast Cells

Figure 1B:
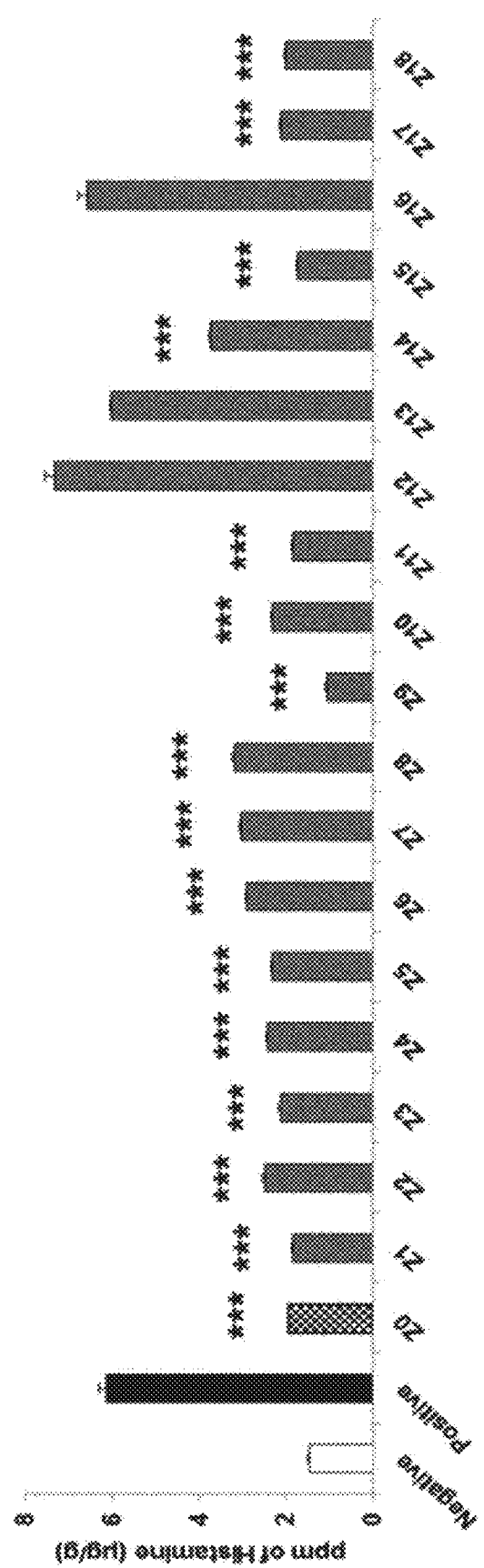

Mast cells (RBL-2H3) were treated with 1 μg/mL of PMA and 1 μg/mL of A23187 as stimulators for 12 hours, and a concentration of histamine released in a cell culture medium was confirmed by ELISA assay. In the experimental groups treated with Z0, Z1 to Z11, Z14, Z15, Z17, and Z18, compared with an experimental group only treated with the stimulators, the histamine concentration was significantly decreased (FIG. 1B).

Example 1-3. Atopic Dermatitis Efficacy Test Using Keratinocytes

Figure 1C:
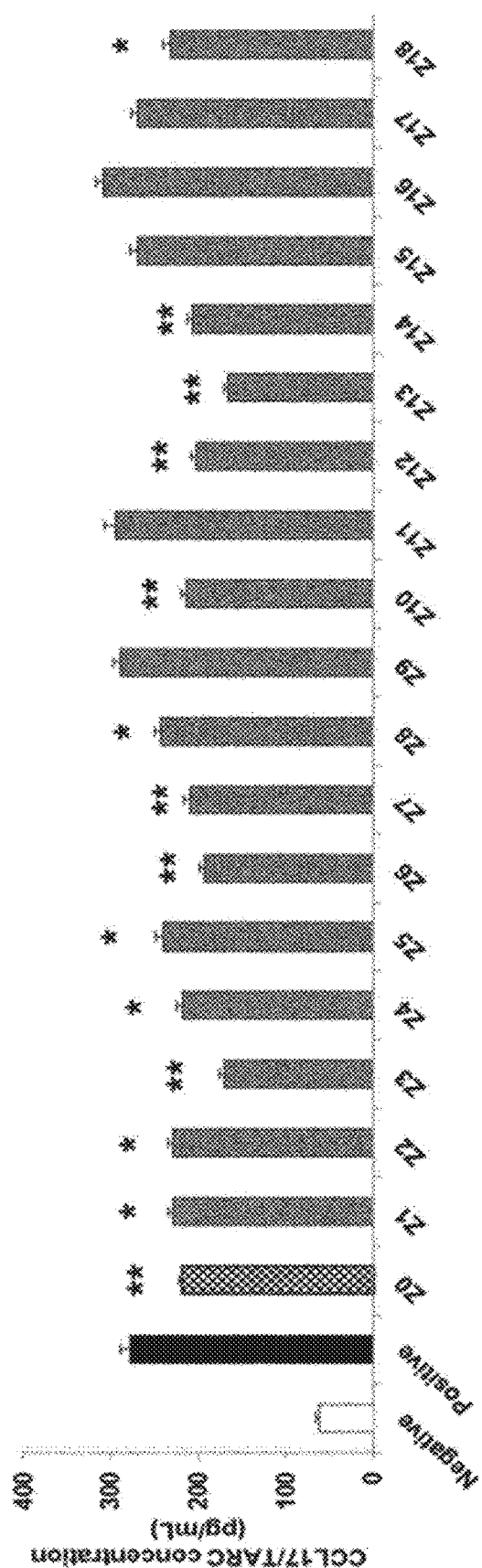

Keratinocytes (HaCaT cells) were treated with 0.4 μg/mL of TNF-α and 0.4 μg/mL of IFN-γ as stimulators for 24 hours, and then a concentration of CCL17/TARC released in a cell culture medium was confirmed by ELISA assay. In the Z0, Z1 to Z8, Z10, Z12 to Z14 and Z18 groups, the CCL17/TARC concentration was significantly decreased (FIG. 1C).

Example 1-4. B Atopic Dermatitis Efficacy Test Using B Lymphocytes

Figure 1D:
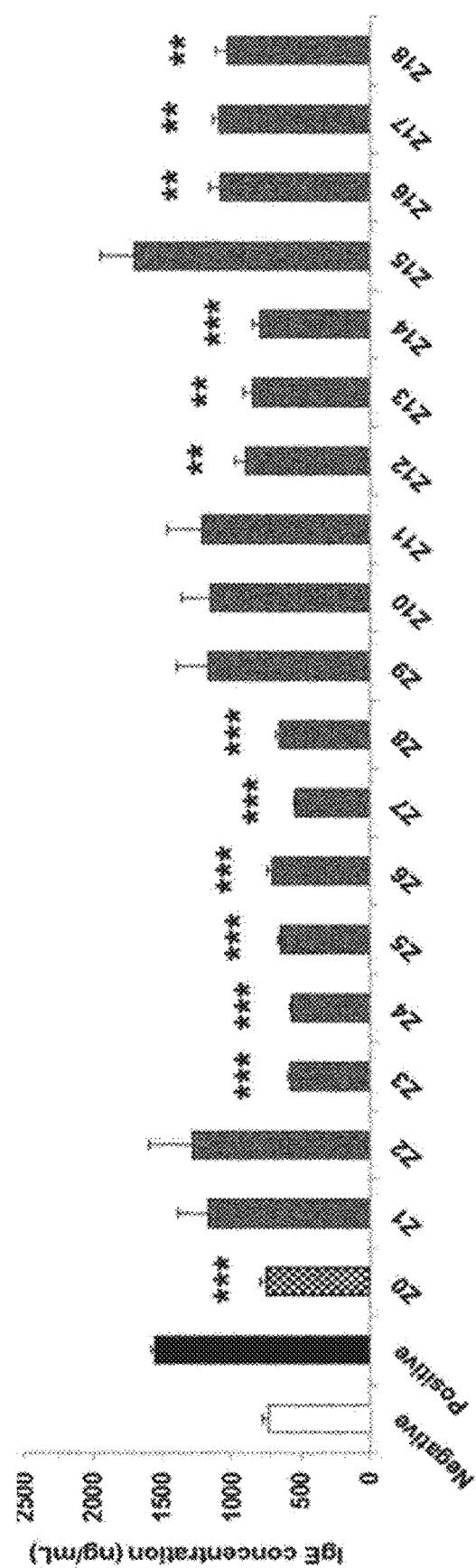

B lymphocytes (RPMI 1788) were treated with 0.1 μg/mL of LPS as a stimulator for 24 hours, and a concentration of IgE released in a cell culture medium was confirmed by ELISA assay. In the Z0, Z3 to Z8, Z12 to Z14 and Z16 to Z18 groups, IgE was significantly decreased (FIG. 1D)

Example 1-5. T Atopic Dermatitis Efficacy Test Using T Lymphocytes

Figure 1E:
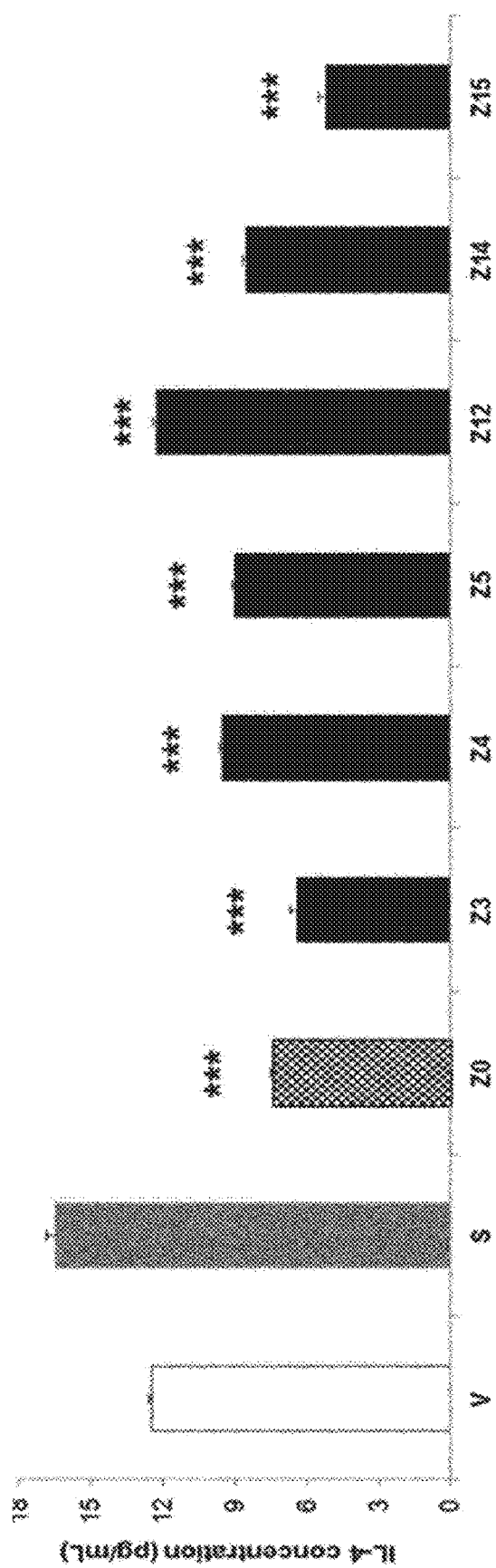

An atopic dermatitis efficacy test using T lymphocytes was performed with six peptide candidate groups (Z3, Z4, Z5, Z12, Z14, and Z15), which were determined to have efficacy from the results of Examples 1-1 to 1-4 described above. T lymphocytes were treated with 50 ng/mL of IL-2 as a stimulator for 12 hours, and a concentration of IL-4 released in a cell culture medium was confirmed by ELISA assay. Here, in the Z3, Z4, Z5, Z12, Z14, and Z15-treated sample groups, IL-4 was significantly decreased (FIG. 1E).

As a result of the atopic dermatitis efficacy test with the five cell lines, the Z3 peptides have efficacy in all cell lines and were confirmed as a material that can be used against atopic dermatitis (Table 3).

TABLE 3

Result of efficacy test for ZAG protein-derived peptides

| target | RAW 264.7 (mouse) IL-6 | RBL-2H3 (rat) Histamine | HaCaT (human) CCL17/ TARC | B lymphocyte (human) IgE | T lymphocyte (human) IL-4 |
|---|---|---|---|---|---|
| Z0 (AZGP1) | • | • | • | • | • |
| Z1 | • | • | • | | |
| Z2 | • | • | • | | |
| Z3 | • | • | • | • | • |
| Z4 | • | • | • | • | • |
| Z5 | • | • | • | • | • |
| Z6 | • | • | • | | |
| Z7 | • | • | • | | |
| Z8 | • | • | • | • | |
| Z9 | • | • | | | |
| Z10(Z1-2) | • | • | • | | |
| Z11(Z2-2) | | • | • | | |
| Z12(Z5-2) | | | • | • | • |
| Z13(Z6-2) | | | • | • | |
| Z14(Z3-2) | • | • | • | | • |
| Z15(Z4-2) | | • | | | |
| Z16(Z4-2) | | | | • | • |
| Z17(Z8-2) | | • | | • | |
| Z18(Z9-2) | | • | | • | • |

Preparation Example 2. Additional Synthesis of ZAG-Derived Peptides

Based on the ZAG3 peptide (ZAG3) selected as the key active site of ZAG having efficacy in the alleviation of atopic symptoms from 18 peptide candidate groups (Z1 to Z18), ZAG3-derived oligopeptides were additionally synthesized (Table 4). Each peptide in Table 4 was synthesized by solid-phase peptide synthesis. It was confirmed by HPLC that the synthesized peptide in the present invention has a purity of 90% or more. The molecular weight of the purified peptide was confirmed by mass spectrometry.

TABLE 4

Peptide candidate groups and amino acid sequences used to identify the active site of ZAG proteins

| Name of peptide | M.W. (g/mol) | Sequence | SEQ ID NO. |
|---|---|---|---|
| Z20mer-1 | 2497.69 | EDWKQDSQLQKAREDIFMET | 20 |
| Z20mer-2 | 2379.68 | DSQLQKAREDIFMETLKDIV | 21 |
| Z20mer-3 | 2492.75 | KAREDIFMETLKDIVEYYND | 22 |
| Z15mer-1 | 1875.98 | EDWKQDSQLQKARED | 23 |
| Z15mer-2 | 1811.02 | DSQLQKAREDIFMET | 24 |
| Z15mer-3 | 1808.14 | KAREDIFMETLKDIV | 25 |
| Z15mer-4 | 1893.16 | IFMETLKDIVEYYND | 26 |

Example 2. Selection of Peptide by In Vitro Atopic Dermatitis Efficacy Test

To select an amino acid sequence having a superior effect from additionally synthesized Z20mer-1, Z20mer-2, Z20mer-3, Z15mer-1, Z15mer-2, Z15mer-3 and Z15mer-4 peptides, an atopic dermatitis efficacy test was performed. Various types of immune cells were treated with each of Z20mer-1, Z20mer-2, Z20mer-3, Z15mer-1, Z15mer-2, Z15mer-3 and Z15mer-4 at a concentration of 1 μg/mL for 24 hours, and then treated with a stimulator suitable for each cell line for the listed time to confirm an immune response. The atopic dermatitis efficacy test method was performed by the same method as described in Example 1 and Table 2.

The experiment was performed with experimental groups: 1) negative control: vehicle-treated group (Neg), 2) positive control: a group treated with only a stimulator (Pos), and 3) experimental group: groups treated with a stimulator and ZAG3 or a ZAG3-derived oligopeptide (Z20mer-1, Z20mer-2, Z20mer-3, Z15mer-1, Z15mer-2, Z15mer-3 or Z15mer-4). Concentrations were measured from cell culture by ELISA.

Example 2-1. Atopic Dermatitis Efficacy Test Using Macrophages

Figure 2A:
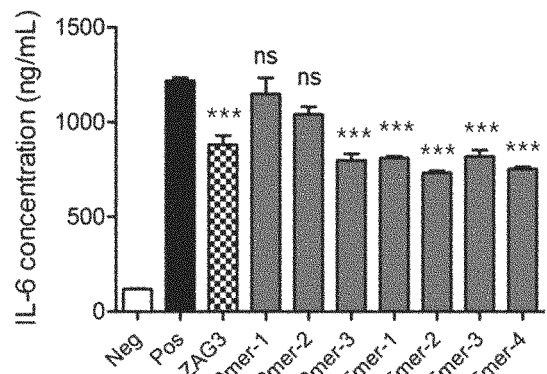
FIGS. 2A, 2B, 2C, 2D and 2E are the results of in vitro efficacy testing of each peptide listed in Table 4 against atopic dermatitis. (a) shows the result for RAW 264.7 macrophages, (b) shows the result for RBL-2H3 mast cells, (c) shows the result for keratinocytes, (d) is the result for B lymphocytes, and (e) shows the result for T lymphocytes.

Macrophages (RAW 264.7 cells) were treated with a stimulator LPS at a concentration of 0.1 μg/mL for 24 hours, and then a concentration of IL-6 released in a cell culture medium was confirmed by ELISA assay. As compared with the positive control (Pos), the IL-6 concentration was significantly decreased in the ZAG3, 20mer-3, 15mer-1, 15mer-2, 15mer-3 and 15mer-4-treated groups (FIG. 2A)

Example 2-2. Atopic Dermatitis Efficacy Test Using Mast Cells

Figure 2B:
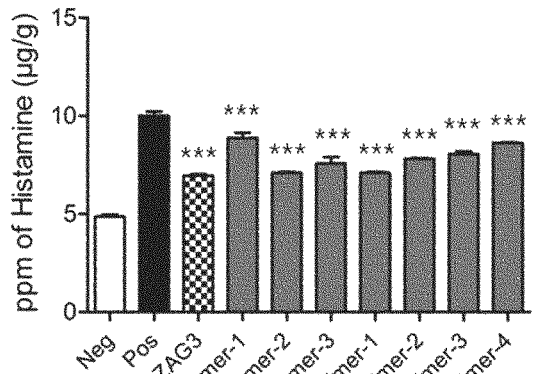

Mast cells (RBL-2H3) were treated with 1 μg/mL of PMA and 1 μg/mL of A23187 as simulators for 12 hours, and then a concentration of histamine released in a cell culture medium was confirmed by ELISA assay. As compared with the positive control (Pos), in all of the oligopeptide-treated groups, the histamine release was reduced (FIG. 2B).

Example 2-3. Atopic Dermatitis Efficacy Test Using Keratinocytes

Figure 2C:
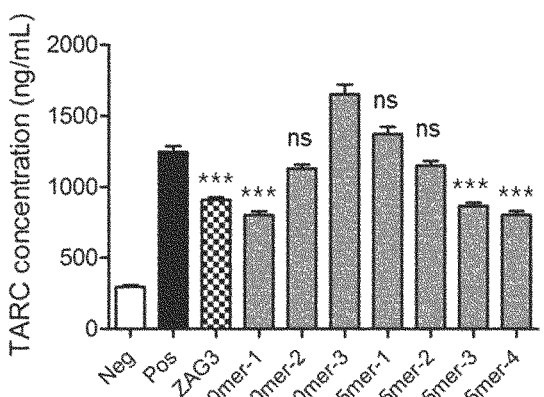

Keratinocytes (HaCaT cells) were treated with 0.4 μg/mL of TNF-α and 0.4 μg/mL of IFN-γ as stimulators for 24 hours, and then a concentration of CCL17/TARC released in a cell culture medium was confirmed by ELISA assay. As compared with the positive control (Pos), the CCL17/TARC concentration was significantly decreased in the ZAG3, 20mer-1, 15mer-3 and 15mer-4-treated groups (FIG. 2C).

Example 2-4. Atopic Dermatitis Efficacy Test Using B Lymphocytes

Figure 2D:
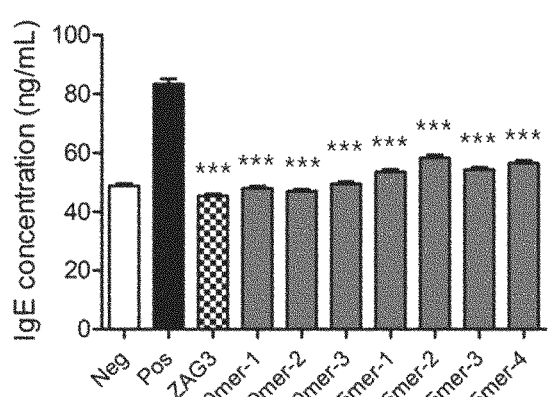

B lymphocytes (RPMI 1788) were treated with 0.1 μg/mL of LPS as a stimulator for 24 hours, and then a concentration of IgE released in a cell culture medium was confirmed by ELISA assay. As compared with the positive control (Pos), in all of the oligopeptide-treated groups, IgE was reduced (FIG. 2D).

Example 2-5. Atopic Dermatitis Efficacy Test Using T Lymphocytes

Figure 2E:
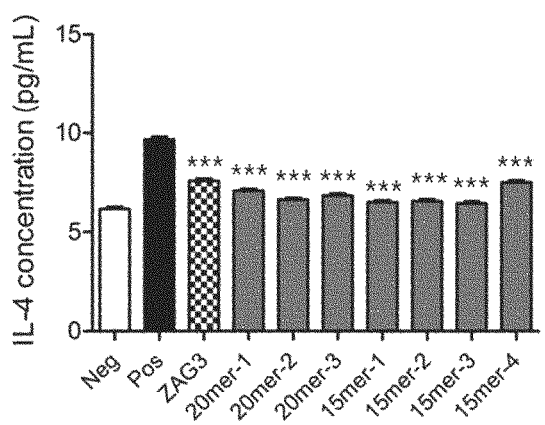

An experiment was performed on T lymphocytes using the target peptides selected through the previous experiment. As compared with the positive control (Pos), in all of the oligopeptide-treated groups (Z20mer-1, Z20mer-2, Z20mer-3, Z15mer-1, Z15mer-2, Z15mer-3, and Z15mer-4), IL-4 was reduced (FIG. 2E).

The test results of the comparative analysis for the efficacy of the total peptide which had been subjected to the atopic dermatitis efficacy test with five types of cell lines have statistical significance, determining as effective, compared with the positive control, and it was confirmed that the peptide is a material that can be used against atopic dermatitis (Table 5).

TABLE 5

Results of efficacy test for ZAG protein-derived peptides

| target | Cell line | | | | |
|---|---|---|---|---|---|
| | RAW 264.7 (mouse) IL-6 | RBL-2H3 (rat) Histamine | HaCaT (human) CCL17/TARC | B lymphocyte (human) IgE | T lymphocyte (human) IL-4 |
| Z20mer-1 | | • | • | • | • |
| Z20mer-2 | | • | | • | • |
| Z20mer-3 | • | • | | • | • |
| Z15mer-1 | • | • | | • | • |
| Z15mer-2 | • | • | | • | • |
| Z15mer-3 | • | • | • | • | • |
| Z15mer-4 | • | • | • | • | • |

What is claimed is:

1. A method of treating or improving inflammation, which comprises administering a therapeutically effective or physiologically effective amount of a zinc-alpha-2-glycoprotein (ZAG) protein-derived peptide to a subject in need thereof, wherein the ZAG protein-derived peptide consists of an amino acid sequence at least 10 and no more than 50 amino acids in lengths, which comprises a fragment of the ZAG protein selected from the group consisting of SEQ ID NOs: 1-18 and 20-26.

2. The method of claim 1, wherein the ZAG protein-derived peptide comprises an amino acid sequence selected from the group consisting of SEQ ID Nos: 3, 21, 22 and 25.

3. The method of claim 1, wherein the ZAG protein-derived peptide consists of an amino acid sequence selected from the group consisting of SEQ ID Nos: 1-18 and 20-26.

4. The method of claim 1, wherein the ZAG protein-derived peptide consists of an amino acid sequence selected from the group consisting of SEQ ID Nos: 3, 21, 22 and 25.

5. The method of claim 1, wherein the ZAG protein-derived peptide is used for inhibiting the inflammation of atopic dermatitis.

6. The method of claim 2, wherein the ZAG protein-derived peptide is used for inhibiting the inflammation of atopic dermatitis.

7. The method of claim 3, wherein the ZAG protein-derived peptide is used for inhibiting the inflammation of atopic dermatitis.

* * * * *

SEQUENCE LISTING

<160> NUMBER OF SEQ ID NOS: 26

<210> SEQ ID NO 1
<211> LENGTH: 30
<212> TYPE: PRT
<213> ORGANISM: Artificial
<220> FEATURE:
<223> OTHER INFORMATION: ZAG protein-derived peptide

<400> SEQUENCE: 1

Gln Glu Asn Gln Asp Gly Arg Tyr Ser Leu Thr Tyr Ile Tyr Thr Gly
1               5                   10                  15

Leu Ser Lys His Val Glu Asp Val Pro Ala Phe Gln Ala Leu
            20                  25                  30

<210> SEQ ID NO 2
<211> LENGTH: 30
<212> TYPE: PRT
<213> ORGANISM: Artificial
<220> FEATURE:
<223> OTHER INFORMATION: ZAG protein-derived peptide

<400> SEQUENCE: 2

Gly Ser Leu Asn Asp Leu Gln Phe Phe Arg Tyr Asn Ser Lys Asp Arg
1               5                   10                  15

Lys Ser Gln Pro Met Gly Leu Trp Arg Gln Val Glu Gly Met
            20                  25                  30

<210> SEQ ID NO 3
<211> LENGTH: 30
<212> TYPE: PRT
<213> ORGANISM: Artificial
<220> FEATURE:
<223> OTHER INFORMATION: ZAG protein-derived peptide

<400> SEQUENCE: 3

Glu Asp Trp Lys Gln Asp Ser Gln Leu Gln Lys Ala Arg Glu Asp Ile
1               5                   10                  15

```
Phe Met Glu Thr Leu Lys Asp Ile Val Glu Tyr Tyr Asn Asp
            20                  25                  30

<210> SEQ ID NO 4
<211> LENGTH: 30
<212> TYPE: PRT
<213> ORGANISM: Artificial
<220> FEATURE:
<223> OTHER INFORMATION: ZAG protein-derived peptide

<400> SEQUENCE: 4

Ser Asn Gly Ser His Val Leu Gln Gly Arg Phe Gly Cys Glu Ile Glu
1               5                   10                  15

Asn Asn Arg Ser Ser Gly Ala Phe Trp Lys Tyr Tyr Asp
            20                  25                  30

<210> SEQ ID NO 5
<211> LENGTH: 30
<212> TYPE: PRT
<213> ORGANISM: Artificial
<220> FEATURE:
<223> OTHER INFORMATION: ZAG protein-derived peptide

<400> SEQUENCE: 5

Gly Lys Asp Tyr Ile Glu Phe Asn Lys Glu Ile Pro Ala Trp Val Pro
1               5                   10                  15

Phe Asp Pro Ala Ala Gln Ile Thr Lys Gln Lys Trp Glu Ala
            20                  25                  30

<210> SEQ ID NO 6
<211> LENGTH: 30
<212> TYPE: PRT
<213> ORGANISM: Artificial
<220> FEATURE:
<223> OTHER INFORMATION: ZAG protein-derived peptide

<400> SEQUENCE: 6

Glu Pro Val Tyr Val Gln Arg Ala Lys Ala Tyr Leu Glu Glu Glu Cys
1               5                   10                  15

Pro Ala Thr Leu Arg Lys Tyr Leu Lys Tyr Ser Lys Asn Ile
            20                  25                  30

<210> SEQ ID NO 7
<211> LENGTH: 30
<212> TYPE: PRT
<213> ORGANISM: Artificial
<220> FEATURE:
<223> OTHER INFORMATION: ZAG protein-derived peptide

<400> SEQUENCE: 7

Leu Asp Arg Gln Asp Pro Pro Ser Val Val Val Thr Ser His Gln Ala
1               5                   10                  15

Pro Gly Glu Lys Lys Lys Leu Lys Cys Leu Ala Tyr Asp Phe
            20                  25                  30

<210> SEQ ID NO 8
<211> LENGTH: 30
<212> TYPE: PRT
<213> ORGANISM: Artificial
<220> FEATURE:
<223> OTHER INFORMATION: ZAG protein-derived peptide

<400> SEQUENCE: 8

Tyr Pro Gly Lys Ile Asp Val His Trp Thr Arg Ala Gly Glu Val Gln
1               5                   10                  15
```

-continued

Glu Pro Glu Leu Arg Gly Asp Val Leu His Asn Gly Asn Gly
                20                  25                  30

<210> SEQ ID NO 9
<211> LENGTH: 30
<212> TYPE: PRT
<213> ORGANISM: Homo sapiens

<400> SEQUENCE: 9

Thr Tyr Gln Ser Trp Val Val Val Ala Val Pro Pro Gln Asp Thr Ala
1               5                   10                  15

Pro Tyr Ser Cys His Val Gln His Ser Ser Leu Ala Gln Pro
                20                  25                  30

<210> SEQ ID NO 10
<211> LENGTH: 30
<212> TYPE: PRT
<213> ORGANISM: Artificial
<220> FEATURE:
<223> OTHER INFORMATION: ZAG protein-derived peptide

<400> SEQUENCE: 10

Gly Leu Ser Lys His Val Glu Asp Val Pro Ala Phe Gln Ala Leu Gly
1               5                   10                  15

Ser Leu Asn Asp Leu Gln Phe Phe Arg Tyr Asn Ser Lys Asp
                20                  25                  30

<210> SEQ ID NO 11
<211> LENGTH: 30
<212> TYPE: PRT
<213> ORGANISM: Artificial
<220> FEATURE:
<223> OTHER INFORMATION: ZAG protein-derived peptide

<400> SEQUENCE: 11

Arg Lys Ser Gln Pro Met Gly Leu Trp Arg Gln Val Glu Gly Met Glu
1               5                   10                  15

Asp Trp Lys Gln Asp Ser Gln Leu Gln Lys Ala Arg Glu Asp
                20                  25                  30

<210> SEQ ID NO 12
<211> LENGTH: 30
<212> TYPE: PRT
<213> ORGANISM: Artificial
<220> FEATURE:
<223> OTHER INFORMATION: ZAG protein-derived peptide

<400> SEQUENCE: 12

Pro Phe Asp Pro Ala Ala Gln Ile Thr Lys Gln Lys Trp Glu Ala Glu
1               5                   10                  15

Pro Val Tyr Val Gln Arg Ala Lys Ala Tyr Leu Glu Glu Glu
                20                  25                  30

<210> SEQ ID NO 13
<211> LENGTH: 30
<212> TYPE: PRT
<213> ORGANISM: Artificial
<220> FEATURE:
<223> OTHER INFORMATION: ZAG protein-derived peptide

<400> SEQUENCE: 13

Cys Pro Ala Thr Leu Arg Lys Tyr Leu Lys Tyr Ser Lys Asn Ile Leu
1               5                   10                  15

```
Asp Arg Gln Asp Pro Ser Val Val Val Thr Ser His Gln
            20                  25                  30

<210> SEQ ID NO 14
<211> LENGTH: 30
<212> TYPE: PRT
<213> ORGANISM: Artificial
<220> FEATURE:
<223> OTHER INFORMATION: ZAG protein-derived peptide

<400> SEQUENCE: 14

Ile Phe Met Glu Thr Leu Lys Asp Ile Val Glu Tyr Tyr Asn Asp Ser
1               5                   10                  15

Asn Gly Ser His Val Leu Gln Gly Arg Phe Gly Cys Glu Ile
            20                  25                  30

<210> SEQ ID NO 15
<211> LENGTH: 30
<212> TYPE: PRT
<213> ORGANISM: Homo sapiens

<400> SEQUENCE: 15

Glu Asn Asn Arg Ser Ser Gly Ala Phe Trp Lys Tyr Tyr Tyr Asp Gly
1               5                   10                  15

Lys Asp Tyr Ile Glu Phe Asn Lys Glu Ile Pro Ala Trp Val
            20                  25                  30

<210> SEQ ID NO 16
<211> LENGTH: 30
<212> TYPE: PRT
<213> ORGANISM: Artificial
<220> FEATURE:
<223> OTHER INFORMATION: ZAG protein-derived peptide

<400> SEQUENCE: 16

Ala Pro Gly Glu Lys Lys Lys Leu Lys Cys Leu Ala Tyr Asp Phe Tyr
1               5                   10                  15

Pro Gly Lys Ile Asp Val His Trp Thr Arg Ala Gly Glu Val
            20                  25                  30

<210> SEQ ID NO 17
<211> LENGTH: 30
<212> TYPE: PRT
<213> ORGANISM: Artificial
<220> FEATURE:
<223> OTHER INFORMATION: ZAG protein-derived peptide

<400> SEQUENCE: 17

Gln Glu Pro Glu Leu Arg Gly Asp Val Leu His Asn Gly Asn Gly Thr
1               5                   10                  15

Tyr Gln Ser Trp Val Val Val Ala Val Pro Pro Gln Asp Thr
            20                  25                  30

<210> SEQ ID NO 18
<211> LENGTH: 30
<212> TYPE: PRT
<213> ORGANISM: Artificial
<220> FEATURE:
<223> OTHER INFORMATION: ZAG protein-derived peptide

<400> SEQUENCE: 18

Ala Val Pro Pro Gln Asp Thr Ala Pro Tyr Ser Cys His Val Gln His
1               5                   10                  15

Ser Ser Leu Ala Gln Pro Leu Val Val Pro Trp Glu Ala Ser
```

<210> SEQ ID NO 19
<211> LENGTH: 298
<212> TYPE: PRT
<213> ORGANISM: Homo sapiens

<400> SEQUENCE: 19

Met Val Arg Met Val Pro Val Leu Leu Ser Leu Leu Leu Leu Leu Gly
1               5                   10                  15

Pro Ala Val Pro Gln Glu Asn Gln Asp Gly Arg Tyr Ser Leu Thr Tyr
            20                  25                  30

Ile Tyr Thr Gly Leu Ser Lys His Val Glu Asp Val Pro Ala Phe Gln
        35                  40                  45

Ala Leu Gly Ser Leu Asn Asp Leu Gln Phe Phe Arg Tyr Asn Ser Lys
    50                  55                  60

Asp Arg Lys Ser Gln Pro Met Gly Leu Trp Arg Gln Val Glu Gly Met
65                  70                  75                  80

Glu Asp Trp Lys Gln Asp Ser Gln Leu Gln Lys Ala Arg Glu Asp Ile
                85                  90                  95

Phe Met Glu Thr Leu Lys Asp Ile Val Glu Tyr Tyr Asn Asp Ser Asn
            100                 105                 110

Gly Ser His Val Leu Gln Gly Arg Phe Gly Cys Glu Ile Glu Asn Asn
        115                 120                 125

Arg Ser Ser Gly Ala Phe Trp Lys Tyr Tyr Tyr Asp Gly Lys Asp Tyr
    130                 135                 140

Ile Glu Phe Asn Lys Glu Ile Pro Ala Trp Val Pro Phe Asp Pro Ala
145                 150                 155                 160

Ala Gln Ile Thr Lys Gln Lys Trp Glu Ala Glu Pro Val Tyr Val Gln
                165                 170                 175

Arg Ala Lys Ala Tyr Leu Glu Glu Cys Pro Ala Thr Leu Arg Lys
            180                 185                 190

Tyr Leu Lys Tyr Ser Lys Asn Ile Leu Asp Arg Gln Asp Pro Pro Ser
        195                 200                 205

Val Val Val Thr Ser His Gln Ala Pro Gly Glu Lys Lys Lys Leu Lys
    210                 215                 220

Cys Leu Ala Tyr Asp Phe Tyr Pro Gly Lys Ile Asp Val His Trp Thr
225                 230                 235                 240

Arg Ala Gly Glu Val Gln Glu Pro Glu Leu Arg Gly Asp Val Leu His
                245                 250                 255

Asn Gly Asn Gly Thr Tyr Gln Ser Trp Val Val Val Ala Val Pro Pro
            260                 265                 270

Gln Asp Thr Ala Pro Tyr Ser Cys His Val Gln His Ser Ser Leu Ala
        275                 280                 285

Gln Pro Leu Val Val Pro Trp Glu Ala Ser
    290                 295

<210> SEQ ID NO 20
<211> LENGTH: 20
<212> TYPE: PRT
<213> ORGANISM: Artificial
<220> FEATURE:
<223> OTHER INFORMATION: ZAG protein-derived peptide

<400> SEQUENCE: 20

Glu Asp Trp Lys Gln Asp Ser Gln Leu Gln Lys Ala Arg Glu Asp Ile
1               5                   10                  15

Phe Met Glu Thr
            20

<210> SEQ ID NO 21
<211> LENGTH: 20
<212> TYPE: PRT
<213> ORGANISM: artificial
<220> FEATURE:
<223> OTHER INFORMATION: ZAG protein-derived peptide

<400> SEQUENCE: 21

Asp Ser Gln Leu Gln Lys Ala Arg Glu Asp Ile Phe Met Glu Thr Leu
1               5                   10                  15

Lys Asp Ile Val
            20

<210> SEQ ID NO 22
<211> LENGTH: 20
<212> TYPE: PRT
<213> ORGANISM: Artificial
<220> FEATURE:
<223> OTHER INFORMATION: ZAG protein-derived peptide

<400> SEQUENCE: 22

Lys Ala Arg Glu Asp Ile Phe Met Glu Thr Leu Lys Asp Ile Val Glu
1               5                   10                  15

Tyr Tyr Asn Asp
            20

<210> SEQ ID NO 23
<211> LENGTH: 15
<212> TYPE: PRT
<213> ORGANISM: Artificial
<220> FEATURE:
<223> OTHER INFORMATION: ZAG protein-derived peptide

<400> SEQUENCE: 23

Glu Asp Trp Lys Gln Asp Ser Gln Leu Gln Lys Ala Arg Glu Asp
1               5                   10                  15

<210> SEQ ID NO 24
<211> LENGTH: 15
<212> TYPE: PRT
<213> ORGANISM: Artificial
<220> FEATURE:
<223> OTHER INFORMATION: ZAG protein-derived peptide

<400> SEQUENCE: 24

Asp Ser Gln Leu Gln Lys Ala Arg Glu Asp Ile Phe Met Glu Thr
1               5                   10                  15

<210> SEQ ID NO 25
<211> LENGTH: 15
<212> TYPE: PRT
<213> ORGANISM: Artificial
<220> FEATURE:
<223> OTHER INFORMATION: ZAG protein-derived peptide

<400> SEQUENCE: 25

Lys Ala Arg Glu Asp Ile Phe Met Glu Thr Leu Lys Asp Ile Val
1               5                   10                  15

<210> SEQ ID NO 26
<211> LENGTH: 15
<212> TYPE: PRT

```
<213> ORGANISM: Artificial
<220> FEATURE:
<223> OTHER INFORMATION: ZAG protein-derived peptide

<400> SEQUENCE: 26

Ile Phe Met Glu Thr Leu Lys Asp Ile Val Glu Tyr Tyr Asn Asp
1               5                   10                  15
```